United States Patent

Dutzmann et al.

Patent Number: 5,198,456
Date of Patent: Mar. 30, 1993

[54] FUNGICIDAL ACTIVE COMPOUND COMBINATIONS

[75] Inventors: Stefan Dutzmann, Hilden; Hans Scheinpflug, Leverkusen; Hans-Ludwig Elbe, Wuppertal, all of Fed. Rep. of Germany

[73] Assignee: Bayer Aktiengesellschaft, Leverkusen, Fed. Rep. of Germany

[21] Appl. No.: 875,504

[22] Filed: Apr. 29, 1992

[30] Foreign Application Priority Data

May 3, 1991 [DE] Fed. Rep. of Germany ....... 4114447

[51] Int. Cl.$^5$ .................. A01N 43/36; A01N 43/64
[52] U.S. Cl. ................................. 514/383; 514/422
[58] Field of Search ............................. 514/383, 422

[56] References Cited

U.S. PATENT DOCUMENTS 3,952,002   4/1976   Kramer et al. ................ 514/383
4,705,800  11/1987   Nyfeler et al. ................ 514/422

Primary Examiner—Allen J. Robinson

[57] ABSTRACT

A new fungicidal composition comprising as active ingredients
A) 1-(4-chlorophenoxy)-3,3-dimethyl-1-(1,2,4-triazol-1-yl)-butan-2-ol of the formula

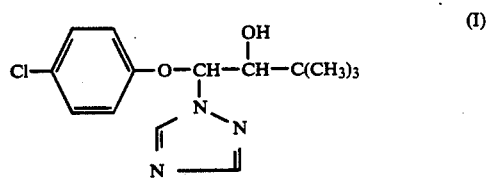

and/or
1-(4-phenyl-phenoxy)-3,3-dimethyl-1-(1,2,4-triazol-1-yl)-butan-2-ol of the formula

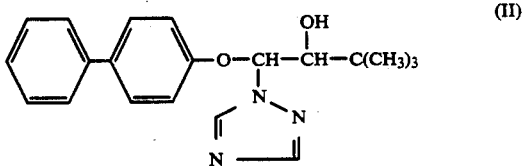

and
B) 4-(2,2-difluoro-1,3-benzodioxol-7-yl)-1H-pyrrole-3-carbonitrile of the formula

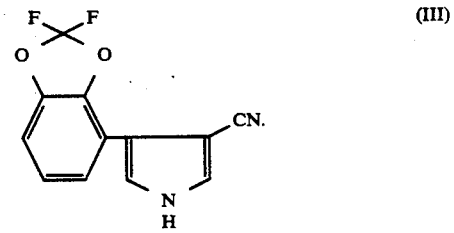

6 Claims, No Drawings

FUNGICIDAL ACTIVE COMPOUND COMBINATIONS

The present application relates to new active compound combinations which consist of the known active compounds 1-(4-chlorophenoxy)-3,3-dimethyl-1-(1,2,4-triazol-1-yl)-butan-2-olor 1-(4-phenyl-phenoxy) triazol-1-yl)-butan-2-ol on the one hand and of the similarly known compound 4-(2,2-difluoro-1,3-benzodioxol-7-yl)-1H-pyrrole-3-carbonitrile on the other hand and are particularly suitable for combating fungi.

It is already known that 1-(4-chlorophenoxy)-3,3-dimethyl-1-(1,2,4-triazol-1-yl)-butan-2-ol and phenyl-phenoxy)-3,3-dimethyl-1-(1,2,4-triazol-1-yl)-butan-2-ol have a fungicidal potency (compare German Patent Specification 2,324,010). The activity of these substances is good; however, when low amounts are applied, it leaves something to be desired in some cases.

It is furthermore already known that 4-(2,2-difluoro-1,3-benzodioxol-7-yl)-1H-pyrrole-3-carbonitrile can be employed for combating fungi (compare EP-OS (European Published Specification) 0,206,999). However, when low amounts are applied, the action of this substance is likewise not always satisfactory.

It has now been found that the new active compound combinations of

A) 1-(4-chlorophenoxy)-3,3-dimethyl-1-(1,2,4-triazol-1-yl)-butan-2-ol of the formula

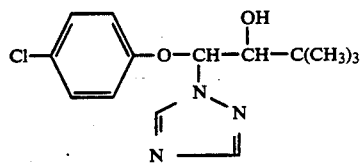

and/or 1- (4-phenyl-phenoxy)-3,3-dimethyl-1-(1,2,4-triazol-1yl)-butan-2-ol of the formula

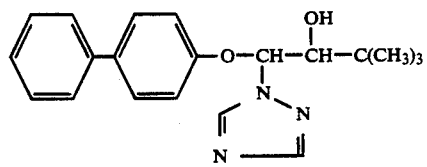

and

B) 4-(2,2-difluoro-1,3-benzodioxol-7-yl)-1H-pyrrole-3-carbonitrile of the formula

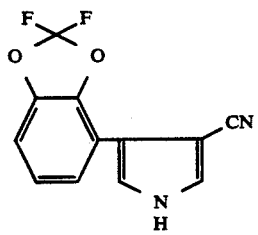

have very good fungicidal properties.

Surprisingly, the fungicidal action of the active compound combinations according to the invention is considerably higher than the sum of the actions of the individual active compounds. A true unforeseeable synergistic effect thus exists, and not merely a supplementary action.

The active compounds contained in the active compound combinations according to the invention are already known (compare German Patent Specification 2,324,010 and EP-OS (European Published Specification) 0,206,999). If the active compounds are present in the active compound combinations according to the invention in certain weight ratios, the synergistic effect manifests itself particularly clearly. However, the weight ratios of the active compounds in the active compound combinations can be varied within a relatively wide range. In general, 0.1 to 2 parts by weight, preferably 0.2 to 1 part by weight, of active compound of the formula (III) are present per part by weight of active compound of the formula (I) and/or (II).

The active compound combinations according to the invention have very good fungicidal properties and can be employed for combating phytopathogenic fungi, such as Plasmodiophoromycetes, Oomycetes, Chytridiomycetes, Zygomycetes, Ascomycetes, Basidiomycetes, Deuteromycetes and the like.

The active compound combinations according to the invention are particularly suitable for combating cereal diseases, such as Fusarium and Drechslera.

The good toleration, by plants, of the active compound combinations in the concentrations required for combating plant diseases permits treatment of above-ground parts of plants, of vegetative propagation stock and seed, and of the soil.

The active compound combinations according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds or active compound combinations with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example lignin-sulphite waste liquors and methylcellulose Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound combinations according to the invention can be present in the formulations as a mixture with other known active compounds, such as fungicides, insecticides, acaricides and herbicides, as well as in mixtures with fertilisers or growth regulators.

The active compound combinations can be used as such or in the form of their formulations or the use forms prepared therefrom, such as ready-to-use solutions, emulsifiable concentrates, emulsions, suspensions, wettable powders, soluble powders and granules.

They are used in the customary manner, for example by watering, spraying, atomising, scattering, brushing on, dry dressing, moist dressing, wet dressing, slurry dressing or encrustation.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The good fungicidal action of the active compound combinations according to the invention can be seen from the following examples. While the individual active compounds have weaknesses in their fungicidal action, the combinations exhibit an action which goes beyond a simple summation of their actions.

A synergistic effect is always present in fungicides if the fungicidal action of the active compound combinations is greater than the sum of the actions of the individually administered active compounds.

EXAMPLE 1

FUSARIUM NIVALE TEST (RYE)/SEED TREATMENT

The active compounds are used as moist or dry dressings.

To apply the dressing, the infected seeds are shaken with the dressing in a closed glass flask for 3 minutes.

2 batches of 100 grains of rye are sown 1 cm deep in standard soil and are cultivated in a greenhouse at a temperature of about 10° C and a relative atmospheric humidity of about 95%, in seedboxes which are exposed to light for 15 hours daily.

The plants are evaluated for symptoms of snow mould about 3 weeks after sowing.

The active compounds, active compound concentrations and test results can be seen from the following table.

TABLE 1

| Active compound | Amount of active compound applied in mg/kg of seed | Degree of action in % of the untreated control |
|---|---|---|
| Fusarium nivale test (rye)/seed treatment | | |
| untreated | — | 0 |
| Known: | | |
| (I) [structure: Cl-phenyl-O-CH-CH-C(CH3)3 with OH and triazole] | 1.5625 | 0 |
| (III) [structure: difluorodioxole fused benzene with pyrrole-CN] | 1.5625 | 35 |
| According to the invention: | | |
| (I) | 0.78125 | |

TABLE 1-continued

| | Fusarium nivale test (rye)/seed treatment | |
|---|---|---|
| Active compound | Amount of active compound applied in mg/kg of seed | Degree of action in % of the untreated control |
| (I) + (III) (1:1) | + 0.78125 | 40 |

EXAMPLE 2

Fusarium culmorum test (wheat)/seed treatment

The active compounds are used as moist or dry dressings.

To apply the dressing, the infected seeds are shaken with the dressing in a closed glass flask for 3 minutes.

2 batches of 100 grains of wheat are sown 1 cm deep in standard soil and are cultivated in a greenhouse at a temperature of about 18° C, in seedboxes which are exposed to light for 15 hours daily.

The plants are evaluated for symptoms about 3 weeks after sowing.

The active compounds, active compound concentrations and test results can be seen from the following table.

TABLE 2-A

| | Fusarium culmorum test (wheat)/seed treatment | |
|---|---|---|
| Active compound | Amount of active compound applied in mg/kg of seed | Degree of action in % of the untreated control |
| — (untreated) | — | =0 |
| Known: | | |
| (I) [structure: Cl-C6H4-O-CH(triazolyl)-CH(OH)-C(CH3)3] | 25 | 36 |
| (III) [structure: difluorobenzodioxole-pyrrole-CN] | 25 | 59 |
| According to the invention: | | |
| (I) + (III) (1:1) | 12.5 + 12.5 | 64 |

TABLE 2-B

| | Fusarium culmorum test (wheat)/seed treatment | |
|---|---|---|
| Active compound | Amount of active compound applied in mg/kg of seed | Degree of action in % of the untreated control |
| — (untreated) | — | =0 |
| Known: | | |
| (II) [structure: biphenyl-O-CH(triazolyl)-CH(OH)-C(CH3)3] | 0.78125 | 15 |

TABLE 2-B-continued

| | Fusarium culmorum test (wheat)/seed treatment | |
|---|---|---|
| Active compound | Amount of active compound applied in mg/kg of seed | Degree of action in % of the untreated control |
| (III) 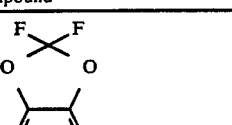 | 0.78125 | 33 |
| According to the invention: | | |
| (II) + (III) (1:1) | 0.390625 + 0.390625 | 44 |

EXAMPLE 3

Drechslera graminea test (barley)/seed treatment (syn. Helminthosporium gramineum)

The active compounds are used as moist or dry dressings. To apply the dressing, the infected seeds are shaken with the dressing in a closed glass flask for 3 minutes.

The seed is embedded in sieved, moist standard soil and exposed in closed Petri dishes to a temperature of 4° C in a refrigerator for 10 days. The germination of the barley and where appropriate also of the fungus spores is initiated by this procedure. 2 batches of 50 grains of the pregerminated barley are then sown 3 cm deep in standard soil and are cultivated in a greenhouse at a temperature of about 18° C, in seedboxes which are exposed to light for 15 hours daily.

The plants are evaluated for symptoms of stripe disease about 3 weeks after sowing.

The active compounds, active compound concentrations and test results can be seen from the following table.

TABLE 3

| | Drechslera graminea test (wheat)/seed treatment (syn. Helminthosporuim gramineum) | |
|---|---|---|
| Active compound | Amount of active compound applied in mg/kg of seed | Degree of action in % of the untreated control |
| — (untreated) | — | =0 |
| Known: | | |
| (I) Cl—⌬—O—CH—CH—C(CH₃)₃ with OH and triazole | 50 | 75 |
| (III) 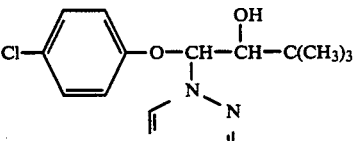 | 50 | 85 |
| According to the invention: | | |
| (I) + (III) (1:1) | 25 + 25 | 92 |

It will be understood that the specification and examples are illustrative but not limitative of the present invention and that other embodiments within the spirit and scope of the invention will suggest themselves to those skilled in the art.

What is claimed is:

1. A fungicidal composition comprising a synergistic fungicidally effective amount of an active compound combination of A) at least one of 1-(4-chlorophenoxy)-3,3-dimethyl-1-(1,2,4-triazol-1-yl)butan-2-ol of the formula

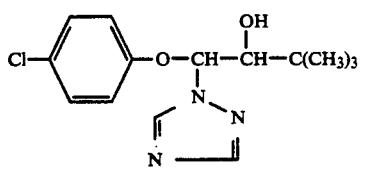
(I)

and
1-(4-phenyl-phenoxy)-3,3-dimethyl-1-(1,2,4-triazol-1-yl)-butan-2-ol of the formula

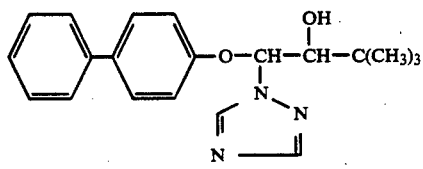
(II)

and
B) 4-(2,2-difluoro-1,3-benzodioxol-7-yl)-1H-pyrrole-3-carbonitrile of the formula

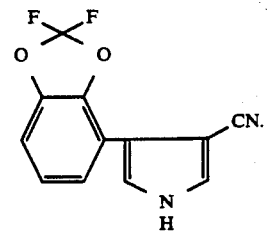
(III)

wherein the synergistic weight ratio of (A) to (B) is between 1:11 and 1:2.

2. A method of combating fungi which comprises applying to such fungi or to a fungus habitat a fungicidally effective amount of an active compound combination according to claim 1.

3. A composition according to claim 1, wherein (A) is (I).

4. A composition according to claim 1, wherein (A) is (II).

5. A composition according to claim 1, wherein (A) is a mixture of (I) and (II).

6. A composition according to claim 1 wherein the weight ratio of (A) to (B) is 1:1.

* * * * *